(12) United States Patent
Morscher et al.

(10) Patent No.: US 9,551,789 B2
(45) Date of Patent: Jan. 24, 2017

(54) SYSTEM AND METHOD FOR QUALITY-ENHANCED HIGH-RATE OPTOACOUSTIC IMAGING OF AN OBJECT

(71) Applicant: Helmholtz Zentrum München Deutsches Forschungszentrum für Gesundheit und Umwelt (GmbH), Neuherberg (DE)

(72) Inventors: Stefan Morscher, München (DE); Vasilis Ntziachristos, Graefelfing (DE); Nikolaos Deliolanis, Stuttgart (DE)

(73) Assignee: Helmholtz Zentrum Munchen Deutsches Forschungszentrum Fur Gesundheit Und Umwelt (GMBH), Neuherberg (DE)

( * ) Notice: Subject to any disclaimer, the term of this patent is extended or adjusted under 35 U.S.C. 154(b) by 220 days.

(21) Appl. No.: 14/141,773

(22) Filed: Dec. 27, 2013

(65) Prior Publication Data
US 2014/0198606 A1 Jul. 17, 2014

Related U.S. Application Data

(60) Provisional application No. 61/752,490, filed on Jan. 15, 2013.

(30) Foreign Application Priority Data

Jan. 15, 2013 (EP) .................... 13000202

(51) Int. Cl.
*G01S 15/89* (2006.01)
*A61B 5/00* (2006.01)
*G01N 21/17* (2006.01)

(52) U.S. Cl.
CPC .............. *G01S 15/89* (2013.01); *A61B 5/0095* (2013.01); *A61B 5/7203* (2013.01);
(Continued)

(58) Field of Classification Search
CPC ... A61B 5/0095; A61B 5/7203; A61B 5/7221; A61B 5/7292; G01N 21/1702; G01S 15/89
(Continued)

(56) References Cited

U.S. PATENT DOCUMENTS

| 4,255,971 A | 3/1981 | Rosenewaig |
| 4,343,993 A | 8/1982 | Bining et al. |

(Continued)

FOREIGN PATENT DOCUMENTS

| EP | 0459392 | 12/1991 |
| EP | 1333703 | 8/2003 |

(Continued)

OTHER PUBLICATIONS

Office Action dated Oct. 6, 2014 for U.S. Appl. No. 13/381,207.
(Continued)

*Primary Examiner* — Daniel L Murphy
(74) *Attorney, Agent, or Firm* — Stoel Rives LLP (57) ABSTRACT

The disclosure relates to systems and methods for optoacoustic imaging of an object comprising, in some embodiments, an image acquisition unit for acquiring a first sequence of tomographic optoacoustic images, the image acquisition unit comprising an illumination device and a detection device configured for repeatedly collecting acoustic waves emerging from the object and for generating the first sequence of tomographic optoacoustic images.

In some embodiments, a processing unit is provided for generating a second sequence of one or more tomographic optoacoustic images from the first sequence of tomographic optoacoustic images based on an analysis of one or more tomographic optoacoustic images of the first sequence of tomographic optoacoustic images and/or at least one property of the object while acquiring the first sequence of
(Continued)

tomographic optoacoustic images and/or at least one property of the acquisition unit while acquiring the first sequence of tomographic optoacoustic images.

26 Claims, 2 Drawing Sheets

(52) U.S. Cl.
CPC .......... *A61B 5/7221* (2013.01); *A61B 5/7292* (2013.01); *G01N 21/1702* (2013.01)

(58) Field of Classification Search
USPC ....................................... 367/7, 11
See application file for complete search history.

(56) References Cited

U.S. PATENT DOCUMENTS

| | | | |
|---|---|---|---|
| 4,385,634 | A | 5/1983 | Bowen |
| 4,646,756 | A | 3/1987 | Watmough et al. |
| 4,770,183 | A | 9/1988 | Groman et al. |
| 4,986,275 | A | 1/1991 | Ishida et al. |
| 5,411,730 | A | 5/1995 | Kirpotin et al. |
| 5,840,023 | A | 11/1998 | Oraevsky et al. |
| 5,924,991 | A | 7/1999 | Hossack et al. |
| 6,070,093 | A | 5/2000 | Oosta et al. |
| 6,102,857 | A | 8/2000 | Kruger |
| 6,173,604 | B1 | 1/2001 | Xiang |
| 6,208,749 | B1 | 3/2001 | Gutkowicz-Krusin et al. |
| 6,216,025 | B1 | 4/2001 | Kruger |
| 6,263,221 | B1 | 7/2001 | Chance et al. |
| 6,424,410 | B1 | 7/2002 | Pelosi |
| 6,428,171 | B1 | 8/2002 | Aoki et al. |
| 6,445,453 | B1 | 9/2002 | Hill |
| 6,477,398 | B1 | 11/2002 | Mills |
| 6,498,492 | B1 | 12/2002 | Rezvani |
| 6,526,298 | B1 | 2/2003 | Khalil et al. |
| 6,567,688 | B1 | 5/2003 | Wang |
| 6,615,063 | B1 | 9/2003 | Ntziachristos et al. |
| 6,641,798 | B2 | 11/2003 | Achilefu et al. |
| 6,662,040 | B1 | 12/2003 | Henrichs et al. |
| 6,700,459 | B2 | 3/2004 | Raihn et al. |
| 6,760,609 | B2 | 7/2004 | Jacques |
| 6,768,265 | B1 | 7/2004 | Ives et al. |
| 7,005,653 | B1 | 2/2006 | O'Connell et al. |
| 7,298,869 | B1 | 11/2007 | Abernathy |
| 7,510,555 | B2 | 3/2009 | Kanzius |
| 7,515,948 | B1 | 4/2009 | Balberg et al. |
| 7,894,885 | B2 | 2/2011 | Bartal et al. |
| 2002/0026106 | A1 | 2/2002 | Khalil et al. |
| 2002/0048077 | A1 | 4/2002 | Fukumoto |
| 2002/0073717 | A1 | 6/2002 | Dean |
| 2002/0163735 | A1 | 11/2002 | Detlef et al. |
| 2002/0193678 | A1 | 12/2002 | Kruger |
| 2003/0023152 | A1 | 1/2003 | Abbink et al. |
| 2003/0135110 | A1 | 7/2003 | Leussier |
| 2004/0054268 | A1 | 3/2004 | Esenaliev et al. |
| 2004/0059265 | A1 | 3/2004 | Candy et al. |
| 2004/0067000 | A1 | 4/2004 | Bates et al. |
| 2004/0127783 | A1 | 7/2004 | Kruger |
| 2004/0176805 | A1 | 9/2004 | Whelan |
| 2004/0181153 | A1 | 9/2004 | Hall |
| 2004/0210126 | A1 | 10/2004 | Hajaj et al. |
| 2004/0232321 | A1 | 11/2004 | Miles et al. |
| 2004/0254457 | A1 | 12/2004 | vander Weide |
| 2005/0150309 | A1 | 7/2005 | Beard |
| 2005/0154308 | A1 | 7/2005 | Quistgaard et al. |
| 2005/0175540 | A1 | 8/2005 | Oraevsky et al. |
| 2005/0234319 | A1 | 10/2005 | Mandelis et al. |
| 2006/0058685 | A1 | 3/2006 | Fomitchov et al. |
| 2006/0064001 | A1 | 3/2006 | Barbour |
| 2006/0084861 | A1 | 4/2006 | Blank et al. |
| 2006/0184042 | A1 | 8/2006 | Wang et al. |
| 2006/0256339 | A1 | 11/2006 | Lowney et al. |
| 2006/0264717 | A1 | 11/2006 | Pesach et al. |
| 2007/0015992 | A1 | 1/2007 | Filkins et al. |
| 2007/0152144 | A1 | 7/2007 | Quake |
| 2007/0197886 | A1 | 8/2007 | Naganuma et al. |
| 2007/0238954 | A1 | 10/2007 | White et al. |
| 2007/0238958 | A1 | 10/2007 | Oraevsky et al. |
| 2007/0274580 | A1 | 11/2007 | Ntziachristos et al. |
| 2008/0071172 | A1 | 3/2008 | Bruck et al. |
| 2008/0118934 | A1 | 5/2008 | Gerdes |
| 2008/0123083 | A1 | 5/2008 | Wang et al. |
| 2008/0173093 | A1 | 7/2008 | Wang et al. |
| 2008/0221647 | A1 | 9/2008 | Chamberland et al. |
| 2008/0228073 | A1 | 9/2008 | Silverman et al. |
| 2009/0024038 | A1 | 1/2009 | Arnold |
| 2009/0038375 | A1 | 2/2009 | Breuer et al. |
| 2009/0054763 | A1 | 2/2009 | Wang et al. |
| 2009/0058746 | A1 | 3/2009 | Delgado |
| 2009/0081122 | A1 | 3/2009 | Rufenacht et al. |
| 2009/0192358 | A1 | 7/2009 | Jaffer et al. |
| 2009/0324048 | A1 | 12/2009 | Leevy |
| 2010/0022866 | A1 | 1/2010 | Feke et al. |
| 2010/0078576 | A1 | 4/2010 | Ntziachristos et al. |
| 2010/0249570 | A1 | 9/2010 | Carson et al. |
| 2011/0001975 | A1 | 1/2011 | Razansky et al. |
| 2011/0040176 | A1 | 2/2011 | Razansky et al. |
| 2011/0201914 | A1 | 8/2011 | Wang et al. |
| 2011/0208057 | A1 | 8/2011 | Oikawa |
| 2011/0231160 | A1 | 9/2011 | Suzuki |
| 2011/0282192 | A1 | 11/2011 | Axelrod et al. |
| 2011/0301453 | A1 | 12/2011 | Ntziachristos et al. |
| 2011/0306857 | A1 | 12/2011 | Razansky et al. |
| 2011/0306865 | A1 | 12/2011 | Thornton et al. |
| 2012/0029829 | A1 | 2/2012 | Li et al. |
| 2012/0123256 | A1 | 5/2012 | Razansky et al. |
| 2012/0150012 | A1 | 6/2012 | Fujimoto et al. |
| 2012/0220851 | A1 | 8/2012 | Razansky et al. |
| 2012/0238873 | A1 | 9/2012 | Lacoste et al. |
| 2013/0041267 | A1 | 2/2013 | Ntziachristos et al. |
| 2013/0312526 | A1 | 11/2013 | Oishi |
| 2014/0114187 | A1 | 4/2014 | Rozental et al. |
| 2014/0198606 | A1 | 7/2014 | Morscher et al. |
| 2014/0336505 | A1 | 11/2014 | Ripoll Lorenzo et al. |
| 2014/0363066 | A1 | 12/2014 | Ntziachristos et al. |

FOREIGN PATENT DOCUMENTS

| | | |
|---|---|---|
| EP | 1561424 | 8/2005 |
| EP | 2695893 | 8/2012 |
| JP | 09219563 | 8/1997 |
| JP | 2004351023 | 12/2004 |
| JP | 2007/307007 | 11/2007 |
| JP | 2010125260 | 6/2010 |
| JP | 2012170762 | 9/2012 |
| WO | WO2004/068405 | 8/2004 |
| WO | WO2006/061829 | 6/2006 |
| WO | WO2006/063246 | 6/2006 |
| WO | WO2007/084771 | 7/2007 |
| WO | WO2007/100937 | 9/2007 |
| WO | WO2007/111669 | 10/2007 |
| WO | WO2008/018082 | 2/2008 |
| WO | WO2008/101019 | 8/2008 |
| WO | WO2009/055095 | 4/2009 |
| WO | WO2010/009747 | 1/2010 |
| WO | WO2011/000389 | 1/2011 |
| WO | WO2011/072198 | 6/2011 |
| WO | WO2011/137385 | 11/2011 |
| WO | WO2012/108170 | 8/2012 |
| WO | WO2012/108172 | 8/2012 |
| WO | WO2012/137855 | 10/2012 |
| WO | WO2012/150721 | 11/2012 |
| WO | WO2013/167147 | 11/2013 |
| WO | WO2013/185784 | 12/2013 |
| WO | WO2014/066150 | 5/2014 |

OTHER PUBLICATIONS

Office Action dated Oct. 29, 2014 for U.S. Appl. No. 13/055,552.
U.S. Appl. No. 13/399,272, filed Nov. 6, 2014, Kellnberger et al.
Office Action dated Nov. 26, 2014 for U.S. Appl. No. 13/386,491.

(56) References Cited

OTHER PUBLICATIONS

Office Action dated Dec. 26, 2014 for U.S. Appl. No. 12/867,265.
Xu et al., 'Universal Back-Projection Algorithm for Photoacoustic Computed Tomography', The American Physical Society,Physical Review, vol. E71, No. 1, pp. 016706, 2005.
Skolnik, Radar Handbook, McGraw Hill, Chapter 8, 2008.
Ye, 'PSTD Method of Thermoacoustic Tomography (TAT) and Related Experimental Investigation', Dissertation, 2009.
Telenkov et al., 'Frequency-Domain Photothermoacoustics: Alternative Imaging Modality of Biological Tissues', Journal of Applied Physics, vol. 105, p. 102029, 2009.
Fan et al., 'Development of a Laser Photothermoacoustic Frequency-Swept System for Subsurface Imaging: Theory and Experiment', J. Acoust. Soc. Am., 116(6), 2004.
Skolnik, Introduction to Radar Systems, Chapter 11.5, McGraw Hill, 1981.
Rosenthal et al., 'Fast Semi-Analytical Model-Based Acoustic Inversion for Quantitative Optoacoustic Tomography', IEEE Transactions on Medical Imaging, vol. 29, No. 6, Jun. 2010.
Baddour, 'Theory and Analysis of Frequency-Domain Photoacoustic Tomography', J. Acoust. Soc. Am., 123(5), pp. 2577-2590, 2008.
Paltauf et al., 'Three-Dimensional Photoacoustic Tomography Using Acoustic Line Detectors', Soc. Opt. Eng., vol. 6437,pp. 1-10, 2007.
Maslov et al., 'Photoacoustic Imaging of Biological Tissue with Intensity-Modulated Continuous-Wave Laser', Journal of Biomedical Optics, vol. 13, No. 2, pp. 024006, 2008.
Kak et al., 'Principles of Computerized Tomographic Imaging', IEEE Press, Chapters 3 and 6, 1988.
International Preliminary Report dated Dec. 24, 2014 for PCT/EP2012/002466.
Wang, 'Multiscale Photoacoustic Microscopy and Computed Tomography', Nature Photonics, Review Article, 2009.
Zhang et al., 'Collecting Back-Reflected Photons in Photoacoustic Microscopy', Optics Express, vol. 18, No. 2, Jan. 18, 2010.
Wang et al., 'Photoacoustic Tomography: In Vivo Imaging from Organelles to Organs', Science, 335(6075), Mar. 23, 2012.
Yao et al.; 'Photoacoustic Tomography: Fundamentals, Advances and Prospects', contrast Media Mol Imaging 6(5), 2011.
Li et al., 'Fast-Scanning Reflection-Mode Integrated Photoacoustic and Optical-coherence Microscopy', Proc. of SPIE, vol, 7564, 2010.
Ntziachristos, 'Going Deeper than Microscopy: The Optical Imaging Frontier in Biology', Nature Methods, vol. 7, No. 8, 2010.
U.S. Appl. No. 14/102,328, filed Dec. 10, 2013, Kacprowicz.
U.S. Appl. No. 14/102,250, filed Dec. 10, 2013, Razansky et al.
Razansky et al., 'Hybrid Photoacoustic Fluorescence Molecular Tomography Using Finite-Element-Based Inversion', Med Phys, Nov. 2007, vol. 34 No. 11, pp. 4293-4301.
Larin et al., 'Monitoring of Tissue Coagulation During Thermotherapy Esing Optoacoustic Technique', Journal of Physics D: Applied Physics, 2005, vol. 38, pp. 2645-2653.
'American National Standard for Safe Use of Lasers', Laser Institute of America, ANS1Z136.1, 2007 (revision of ANS1Z136.1 2000).
Laufer et al., 'Quantitative Spatially Resolved Measurement of Tissue Chromophore Concentrations Using Photoacoustic Spectroscopy: Application to the Measurement of Blood Oxygenation and Haemoglobin Concentration', Phys Med Biol, 2007, vol. 52, pp. 141-168.
Chen et al., 'Atomic Decomposition by Basis Pursuit', SIAM Review, 2001, vol. 43 No. 1, pp. 129-159.
Jetzfellner et al., 'Preformance of Interactive Optoacoustic Tomography with Experimental Data', Applied Physics Letters, 2009, vol. 95, pp. 013703.1-013703.3.
Cox et al., 'Gradient-Based Quantitative Photoacoustic Image for Molecular Imaging', Proc of SPIE, 2007, vol. 6437, pp. 6431T.1-6431T.10.
Cox et al., 'Two-Dimensional Quantitative Photoacoustic Image Reconstruction of Absorption Distributions in Scattering Medica by Use of a Simple Iterative Method', Applied Optics, Mar. 10, 2006, vol. 45 No. 8, pp. 1866-1873.
Paltauf et al., 'Iterative Reconstruction Algorithm for Optoacoustic Imaging', J Acoust Soc Am, Oct. 2002,vol. 112 No. 4, pp. 1536-1544.
Jiang et al., 'Spatially Varying Optical and Acoustic Property Reconstruction Using Finite-Element-Based Photoacoustic tomography', J Opt Soc Am, Apr. 2006, vol. 23 No. 4, pp. 878-888.
Intes et al. 'Projection Access Order in Algebraic Reconstruction Technique for Diffuse Optical Tomography', Phys Med Biol, 2002, vol. 47, pp. N1-N10.
Office Action dated Dec. 7, 2012 for U.S. Appl. No. 13/055,552.
Vinegoni et al., 'In vivo Imaging of *Drosophila metanogaster* Pupae with Mesoscopic Fluorescence Tomography', Nature Methods, Jan. 2008, vol. 5 No. 1, pp. 45-47 and Supplementary Notes.
Zacharakis et al., 'Volumetric Tomography of Fluorescent Proteins Through Small Animals In Vivo', PNAS, Dec. 20, 2005, vol. 102 No. 51, pp. 18252-18257.
Capps, "Near Field or Far Field?", EDN Network, www.ednmag.con Aug. 16, 2001, p. 95-102.
Office Action dated Jun. 3, 2013 for U.S. Appl. No. 12/867,265.
Office Action dated Jun. 18, 2013 for U.S. Appl. No. 13/055,552.
Office Action dated Aug. 2, 2013 for U.S. Appl. No. 13/386,491.
Yuan et al., 'Quantitative Photoacoustic Tomography: Recovery of Optical Absorption coefficient Maps of Haterogeneous Media', Applied Physics Letters 88:231101, 2006.
Razansky et al., 'Multispectral Photoacoustic Imaging of Fluorochromes in Small Animals', Optics Letters, vol. 32, No. 19, pp. 2891-2893, Oct. 1, 2007.
Rosenthal et al., 'Quantitative Optoacoustic Signal Extraction Using Sparse Signal Repesentation', IEEE Transactions on Medical Imaging, vol. 28, No. 12, pp. 1997-2006, 2009.
Xu et al., 'Exact Frequency-Domain Reconstruction for Thermoacoustic Tomography—I: Planar Geometry', IEEE Transactions on Medical Imaging, vol. 21, No. 7, pp. 823-828, 2002.
Oraevsky et al., 'Direct Measurement of Laser Fluence Distribution and Optoacoustic Imaging in Heterogeneous Tissues', Proc SPIE 2323, Laser Interactions with Hard and Soft Tissue 11, 37, 1995.
Karabutov et al., 'Optoacoustic Measurement of Optical Properties of Turbid Media', Proc. SPIE vol. 4749, pp. 288-298, 2002.
Razansky et al., 'Multispectral Opto-Acoustic Tomography of Deep-Seated Fluorescent Proteins in Vivo', Nature Photonics, 3, 412-417, 2009.
Schulz et al., 'Experimental Fluorescence Tomography of Tissues with Noncontact Measurements', IEEE Transactions on Medical Imaging, vo. 23, No. 4, 492-500, 2004.
Ripoll et al., 'Free-Space Propagation of Diffuse Light: Theory and Experiments', Phys. Rev, Lett., vol. 91, No. 10, pp. 103901-1-103901-6, 2003.
Zibulevsky et al., 'Blind Source Separation by Sparse Decomposition', ICA, Principle and Practice, Chapter 7, Cambridge, 2001.
Office Action dated Jan. 14, 2014 for U.S. Appl. No. 13/055,552.
Office Action dated Jan. 29, 2014 for U.S. Appl. No. 12/867,265.
Sugiyama et al., 'Character Pattern Recognition Utilizing Independent Component', Proceedings of the 44th Conference of the Institute of Systems, Control and Information Engineers (ISCIE), p. 457-458, English abstract, 2000.
Taruttis et al., 'Motion Clustering for Deblurring Multispectral Optoaxoustic Tomography Images of the Mouse Heart', Journal of Biopmedical Optics, vol. 17, No. 1, pp. 16009-1 to 16009-4, Jan. 2012.
Taruttis et al., 'Imaging the Small Animal Cardiovascular System in Real-Time with Multispectral Optoacoustic Tomography', Proc of SPIE, vol. 7899, pp. 789913-1 to 789913-8, 2011.
Buehler et al., 'Video Rate Optoacoustic Tomography of Mouse Kidney Perfusion', Optics Letters, vol. 35, No. 14, pp. 2475-2477, Jul. 15, 2010.
Glatz et al., 'Blind Source Unmixing in Multi-Spectral Optoacoustic Tomography', Optics Express, vol. 19, No. 4, pp. 3175-3184, Feb. 14, 2011.

(56) References Cited

OTHER PUBLICATIONS

Morscher et al., 'Spectral Unmixing Using Component Analysis in Multispectral Optoacoustic Tomography', Proc SPIE, vol. 8089, 2011.
Morscher et al., 'Blind Spectral Unmixing to Identify Molecular Signatures of Absorbers in Multispectral Optoacoustic Tomography', Proc SPIE, Photons Plus Ultrasound: Imaging and Sensing, vol. 7899, 2011.
Office Action dated Jul. 31, 2014 for U.S. Appl. No. 13/386,491.
Ku et al., 'Thermoacoustic and Photoacoustic Tomography of Thick Biologial Tissues Toward Breast Imaging', Technogy in Cancer Research & Treatment, ISSN 1533-0346, vol. 4, No. 5, dated Oct. 2005.
Aguirre et al., 'A curved Array Photoacoustic Tomography System for Small Animal Imaging', Proc, SPIE 6437:OV1-OV10, 2007.
Allen et al., 'Dual Wavelength Laser Diode Excitation Source for 2D Photoacoustic Imaging', Proc. SPIE 6437: U1-U9, 2007.
Erpelding et al., 'Three-Dimensional Photoacoustic Imaging with a Clinical Two-Dimensional Matrix Ultrasound Transducer', Photons Plus Ultrasound: Imaging and Sensing, Proc of SPIE, vol. 7899, 2011.
Office Action dated Jan. 28, 2014 for U.S. Appl. No. 13/386,491.
Office Action dated May 7, 2015 for U.S. Appl. No. 13/381,207.
Office Action dated Jul. 7, 2015 for U.S. Appl. No. 13/386,491.
Office Action dated Jul. 14, 2015 for U.S. Appl. No. 14/102,250.
Office Action dated Jul. 14, 2015 for U.S. Appl. No. 14/102,328.
Office Action dated Jul. 30, 2015 for U.S. Appl. No. 13/055,552.
Office Action dated Aug. 30, 2012 for U.S. Appl. No. 12/684,816.
Office Action dated Oct. 2, 2015 for U.S. Appl. No. 12/867,265.
Pratt, 'Image Sampling and Reconstruction,' Digital Image Processing: PIKS Scientific Inside by William K. Pratt, pub. Wiley-Interscience; 4 Edition (Feb. 9, 2007); ISBN: 0471767778; Chapter 4.
Song, 'High-Speed Photoacoustic Microscopy in Vivo', Ph.D. Thesis, School of Eng. & Appl. Sci., Washington University, Saint Louis, 133 pgs, 2010.
Viator et al., 'Clinical Testing of a Photoacoustic Probe for Port-Wine Stain Depth Determination', Lasers Surg. Med. 30:141-148, 2002.
Ash et al., 'Super-Resolution Aperture Scanning Microscope', Nature, vol. 237, pp. 510-512, Jun. 30, 1972.
Final Office Action dated Jan. 21, 2016 for U.S. Appl. No. 14/102,328.
Philips. White Pate for iU22 with X7-2 Probe, 2010, 1 pg, internet. https://web/archive.org/web/20100908015304/http://healthcare.philips.com/main/products/ultrasound/transducers/7x_2.wpd.
Skolnik, Introduction to Radar Systems, Chapter 6.5, McGraw Hill, 2001.
Yin et al., 'Tomographic Imaging of Absolute Optical Absorption Coefficient in Turbid Media Using Combined Photoacoustic and Diffusing Light Measurements', Optics Letters, vol. 32 No. 17, pp. 2556-2558, 2007.
Final Office Action dated Feb. 19, 2016 for U.S. Appl. No. 14/102,250.
Xu, et al., "Time-Domain Reconstruction for Thermoacoustic Tomography in a Spherical Geometry", IEEE Transactions on Medical Imaging vol. 21, No. 7, Jul. 2002, pp. 814-822.
Final Office Action dated Mar. 9, 2016 for U.S. Appl. No. 13/386,491.
Office Action dated Mar. 11, 2016 for U.S. Appl. No. 13/055,552.
U.S. Appl. No. 14/102,328, Non-Final Office Action, Aug. 26, 2016, 29 pages.
U.S. Appl. No. 13/386,491, Non-Final Office Action, Sep. 23, 2016, 54 pages.
U.S. Appl. No. 13/055,552, Notice of Allowance, Nov. 18, 2016, 13 pages.

Fig. 1

SYSTEM AND METHOD FOR QUALITY-ENHANCED HIGH-RATE OPTOACOUSTIC IMAGING OF AN OBJECT

RELATED APPLICATIONS

This application claims priority to U.S. Provisional Application No. 61/752,490 filed on Jan. 15, 2013 and to European Patent Application 13 000 202.5, filed on Jan. 15, 2013, both of which are hereby incorporated by reference in their entireties.

TECHNICAL FIELD

The present disclosure relates to a system and method for optoacoustic imaging of an object.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Optoacoustic imaging is based on the photoacoustic effect, according to which ultrasonic waves are generated due to absorption of electromagnetic radiation by an object, e.g. a biological tissue, and a subsequent thermoelastic expansion of the object. Excitation radiation, for example laser light, can either be pulsed radiation with very short pulse durations or continuous radiation with a modulated amplitude or frequency.

Using tomographic reconstruction with a view from multiple projections allows for a generation of a full view of the sample, enabling imaging based on optical absorption of both intrinsic and extrinsic tissue chromophores for biomedical imaging.

Therefore, in contrast to conventional optical imaging, fluorescence or light emission in general are not prerequisites for generating contrast in optoacoustic imaging. One characteristic of the process is that heavy scattering present in biological tissues does not obscure the spatial resolution, because the detected phenomena are sound waves that are far less disturbed by tissue due to the lower frequency.

Optoacoustic resolution may be limited by the focusing and detection band of the ultrasound transducer and the frequency-dependent acoustic attenuation. At the same time, optoacoustics may provide a high, wavelength-dependent penetration depth of up to several centimeters within the near-infrared optical imaging window (650 to 950 nm) or other suitable wavelengths.

By imaging absorbance at multiple excitation wavelengths, multispectral optoacoustic tomography (MSOT) can provide molecular specificity to reveal absorbers with distinct spectral absorbance.

In contrast to optical imaging, in ultrasound and also optoacoustic imaging the information required to create an image is generated within a very short time after the absorption of a single pulse. While both sensitivity and signal to noise ratio (SNR) in optical imaging can be increased by increasing exposure time, ultrasonic and also optoacoustic imaging may involve a repetition of the acquisition process to compensate for noise and SNR. On the other hand, this promotes the ability of optoacoustic imaging to capture very fast processes at a repetition rate that is only limited by the source of illumination and the performance of the signal acquisition system. Furthermore, a final optoacoustic image already represents the full reality and does not necessarily require any additional, corrective measurements to compensate for, e.g., auto-fluorescence of tissue or similar.

Signal acquisition in optoacoustics may be done using ultrasound transducers or hydrophones. In some implementations, a single transducer is rotated around a sample in order to create a tomographic view of the sample. Thus, in some instances, to acquire optoacoustic images at a high rate, an ultrasound transducer array may be employed, the array may allow for acquiring sufficient data to reconstruct an image without moving the transducer to enable capturing a static setting. With hybrid approaches being very well feasible, detection geometries in optoacoustics can be divided into arc or bowl shape approaches and linear geometries. Depending on the desired characteristics, detectors can either be shaped to predominantly detect signals from a two dimensional plane or a three dimensional volume.

Similar to ultrasound, noise influences in the reconstructed image may contain contributions of both systemic and thermal noise as well as other, extrinsic sources that are received in the analog chain before AD conversion of the acquired signal.

Based on the aforementioned setting, each individual acquisition is perturbed by a certain amount of noise that determines the overall noise level of a system. Whilst measures in hardware and system design (such as shielding of setting and cables) can be taken to reduce significant external sources, a lot of parasitic signals will still be measured by the analog part of the detection chain. For clinical imaging, the exposure threshold of skin is regulated by the FCC dependent on repetition rate and exposed area, so the signal and thus signal to noise ratio (SNR) cannot be improved by increasing laser power. Moreover, in general, in images which are based on multiple images acquired for one setting, the SNR and resulting perturbations by noise increase. Based on these perturbations, noise reduction algorithms may need to be applied to improve the quality of acquired images.

Exemplary applications for optoacoustic imaging are in the field of imaging of endogenous contrast in tissue. In the predominantly used near-infrared domain the key absorbers are hemoglobin and melanin, providing a unique anatomical contrast without any additional agents. Using multispectral acquisition for functional and molecular imaging, individual absorbers can be separated and quantified, allowing e.g. for blood oxygen saturation measurements and detecting necrosis. Another clinically relevant example is detecting melanin content in lymph nodes for cancer diagnosis.

The number of applications is even increased by using exogenous contrast agents such as fluorescent dyes as known from optical imaging, activatable probes, fluorescent proteins or nanoparticles. They can be targeted to specific sites using functional groups, where even different numbers of optoacoustic absorbers can be combined to even simultaneously track different processes.

There are a number of applications which may benefit from a high actual image rate. In motion-rich settings, an acquisition relying on averaging is likely to produce blurry images that need to be co-registered for multispectral analysis, while an image resulting from a single frame acquisition will suffer from a relatively high noise level. One example for such a setting is imaging of small vasculature with the diameter approaching the spatial resolution, where averaging will blur tiny features. The same applies for imaging of fast kinetic processes in an organism, where averaging shadows fast changes. Other examples include monitoring an arterial input function of an injected substance, tissue perfusion measurements, blood flow imaging, drug delivery monitoring and pharmacokinetic modeling.

The present disclosure is based on the problem to provide a system and method for optoacoustic imaging allowing for an acquisition of sequences of tomographic optoacoustic images of high image frame rate and high image quality, for example, video sequences of tomographic optoacoustic images exhibiting less motion and/or noise perturbations than conventional video sequences.

This problem is addressed by the system and method according to the present disclosure.

A system for optoacoustic imaging of an object according to the present disclosure may comprise an image acquisition unit for acquiring a first sequence of tomographic optoacoustic images of a region of interest of the object, wherein the image acquisition unit comprises an illumination device for repeatedly emitting electromagnetic radiation to the region of interest of the object and a detection device for repeatedly collecting acoustic waves emerging from the object upon excitation of the object and for generating the first sequence of tomographic optoacoustic images of the region of interest from the repeatedly collected acoustic waves. The system may further comprise a processing unit for generating a second sequence of one or more tomographic optoacoustic images from the first sequence of tomographic optoacoustic images based on an analysis of one or more tomographic optoacoustic images of the first sequence of tomographic optoacoustic images and/or at least one property of the object while acquiring the first sequence of tomographic optoacoustic images and/or at least one property of the acquisition unit while acquiring the first sequence of tomographic optoacoustic images.

A method for optoacoustic imaging of an object according to the present disclosure may comprise acquiring a first sequence of tomographic optoacoustic images of a region of interest of the object by irradiating the region of interest of the object with electromagnetic radiation and repeatedly collecting acoustic waves emerging from the object upon irradiating the object and generating the first sequence of tomographic optoacoustic images of the region of interest from the repeatedly collected acoustic waves. The method may further comprise generating a second sequence of one or more tomographic optoacoustic images from the first sequence of tomographic optoacoustic images based on an analysis of one or more tomographic optoacoustic images of the first sequence of tomographic optoacoustic images and/or at least one property of the object while acquiring the first sequence of tomographic optoacoustic images and/or at least one property of the irradiation of the object and/or the collection of acoustic waves while acquiring the first sequence of tomographic optoacoustic images.

In the following, the term "tomographic optoacoustic image" will be also referred to as "image" for reasons of simplification. Further, the term "sequence of tomographic optoacoustic images" will be also referred to as "video" or "video sequence" or "video stream". Moreover, the term "electromagnetic radiation" in the sense of the present disclosure relates to any electromagnetic radiation by means of which acoustic waves or pulses can be generated in an object under investigation upon irradiating the object. The term "electromagnetic radiation" relates to visible light and/or non-visible light, e.g. in the infrared or ultraviolet spectral range, but also includes radio frequency radiation and/or microwave radiation.

The solution according to the present disclosure is based on the approach to acquire a first sequence of images from a region of interest of the object and to derive a second image or a second sequence of images from the first sequence of images, for example, by processing the first sequence of images, wherein the derivation or generation of the second image or second sequence of images from the first sequence of images depends on information relating to one or more images of the first sequence of images and/or information relating to the object or the acquisition unit or acquisition process while the first sequence of tomographic images is acquired. For example, the information relating to one or more images of the first sequence of images is obtained by an analysis of the one or more images of the first sequence. In some embodiments, information relating to the object reflects properties of time-variant processes of the object or within the object, like respiration, heartbeat or blood flow, while the images of the first sequence of images are acquired from the object. Likewise, information relating to the acquisition unit or acquisition process reflects parameters of the acquisition process under which images of the first sequence of images are acquired, for example the intensity of the electromagnetic radiation that excites the object, for example, the irradiation laser power.

In some embodiments, based on the dependence of the strength of the optoacoustic signal on incident irradiation power, such as light intensity, the acquired signals and/or images have to be or can be corrected for wavelength-dependent light fluence in tissues in order to obtain quantitative images. Depending on the complexity of the setting, this can be done by using a generic map of light fluence or an individual map configured to the situation before image reconstruction on the acquired signals, or after the image reconstruction on the final image.

By means of the approach according to the present disclosure it is possible to significantly improve the quality of the originally acquired first sequence of images, e.g. by suppressing motion-related effects or noise perturbations. At the same time, a high frame rate of the improved video images is achieved or maintained, wherein the frame rate of the second sequence of images is not or not considerably reduced compared to the original frame rate of the first sequence of images. Moreover, the spatial resolution of the images of the second sequence is not or not significantly reduced compared to the resolution of the images of the first sequence. As a result, by means of the present disclosure it is possible to record and playback an improved (second) video sequence of a particular phenomenon on or within the object. Further, the present disclosure allows for a quantitation of results and an analysis of dynamic and pharmacokinetic parameters in order to provide a powerful biological research platform that outperforms established imaging modalities.

In summary, by means of the present disclosure high image rate, such as real-time, optoacoustic images are obtained which allow for acquiring images of fast processes in vivo with high resolution and significantly reduced influences of noise and motion. In this way, the present disclosure allows for studying anatomy, molecular contrast and fast processes in biological tissues by adding the temporal dimension to existing optoacoustic imaging approaches.

According to an embodiment of the present disclosure, the at least one property of the object relates to temporal, such as, periodic, changes at or within the object, such as, due to respiration, pulse or blood flow, while acquiring the first sequence of tomographic optoacoustic images. In some embodiments, the at least one property of the object is acquired by means of an external device, which may be configured for observing temporal changes at or within the object, such as due to respiration, pulse or blood flow. By monitoring a property or properties of the object while the image acquisition process, information on relevant time-variant processes within the object can be obtained. The obtained information can be considered in the processing step in which the second sequence of images is derived from the first sequence of images such that, e.g., motion-related effects or artifacts due to respiration, heartbeat or blood flow in the images of the first sequence can be eliminated when deriving the second sequence of images. In this way, motion-related artifacts in the images can be eliminated or at least significantly reduced easily and reliably.

Alternatively or additionally, the at least one property of the object is derived from one or more tomographic optoacoustic images of the first sequence of tomographic optoacoustic images. For example, the first sequence of images is analyzed with respect to recurring, such as periodic, variations or movements, e.g. a movement of the heart or chest, available in the images. Based on this analysis, the effects of the identified variations or movements on the images are eliminated or at least reduced subsequently. By means of this embodiment, motion-related artifacts in the images can be eliminated or at least significantly reduced in a particularly easy and reliable manner.

According to a further embodiment, the acquisition unit is configured to be controlled by control signals from, wherein the control signals are generated by the processing unit and/or by an external device, which is, for example, configured for observing a time-variant process in the object, such as respiration, heartbeat or blood flow of the object, to allow for an acquisition of the first sequence of tomographic optoacoustic images at specific instants, such as at less motion-perturbed instants, e.g., at timeframes with no respiratory activity or certain periods of the heart cycle. By mean of this, e.g., possible motion-related artifacts or noise perturbations in the images can be avoided or at least reduced significantly ab initio. Therefore, this embodiment represents a very efficient way to obtain high-rate video images of the object with reduced or eliminated motion and/or noise perturbations.

In some embodiments, the processing unit is configured for generating the second sequence of tomographic optoacoustic images based on an analysis of a subsequence of tomographic optoacoustic images of the first sequence of tomographic optoacoustic images. A subsequence of images may comprise at least two consecutive tomographic optoacoustic images of the first sequence of tomographic optoacoustic images or may comprise at least two tomographic optoacoustic images of the first sequence which are spaced apart by one or more further images. By analyzing a subsequence of the first sequence of images more relevant information may be obtained in order to remove, e.g., motion-related effects when the second sequence of images is derived from the first sequence of images. Thus, a high-rate second sequence of images with reduced or eliminated motion-related perturbations can be obtained in a very reliable and simple manner.

In some embodiments the processing unit is configured for generating the second sequence of tomographic optoacoustic images based on an analysis of a quality of one or more tomographic optoacoustic images of the first sequence of tomographic optoacoustic images.

According to a further embodiment of the present disclosure, the processing unit is configured for generating the second sequence of tomographic optoacoustic images based on an analysis of tomographic optoacoustic images of the first sequence of tomographic optoacoustic images with respect to their individual properties, for example, signal-to-noise ratio, contrast, blur, sharpness or histogram. Based on the result of this analysis, each of the analyzed images is processed, for example, improved, or assessed in the processing unit before the second sequence of images is derived from these images. When assessing the images it can be decided whether to keep and to include an image or a weighted version of the image into the second sequence of images or to discard the image. This is a very efficient way to achieve a high image quality of the second sequence of images without significantly reducing the high frame rate of the original sequence.

In some embodiments, the processing unit is configured for generating the second sequence of tomographic optoacoustic images from the first sequence of tomographic optoacoustic images based on an analysis of properties, such as, signal-to-noise ratio, frequency spectrum or noise patterns, of the repeatedly collected acoustic waves prior to generating the first sequence of tomographic optoacoustic images from the repeatedly collected acoustic waves. Other than in the above-mentioned embodiment, in which the already reconstructed images of the first sequence are analyzed, in this embodiment the so-called raw data, i.e. the ultrasound detector signals corresponding to the repeatedly detected acoustic waves, are analyzed. By means of analyzing the raw data of the images information can be obtained which would be—due to the reconstruction step—no longer present in the reconstructed images of the first sequence of images. Thus, this embodiment allows for an efficient and reliable elimination or reduction of motion- and/or noise-related perturbations in the images.

Alternatively or additionally, the processing unit is configured for generating the second sequence of tomographic optoacoustic images based on an analysis of tomographic optoacoustic images of the first sequence of tomographic optoacoustic images regarding properties of the tomographic optoacoustic images with respect to each other, for example with respect to a similarity of the images, a correlation of the images, a standard deviation or k-means. By means of analyzing images, for example a subsequence of images, of the first sequence of images with respect to each other, further additional information is obtained which is not contained in each of the individual images alone. In some embodiments, this relates to the desire of separating the information contained in the images of the first sequence of images from the contained perturbing influences of noise and motion. By considering this additional information when a second sequence of images is derived from the first sequence of images, the quality of the individual images can be increased, resulting in a particularly high image quality and video rate of the second sequence of images. The upper bound to the improvement of quality is given by the identification of the overall information contained in the analyzed subsequence of images as compared to the noise contained in the images of the analyzed subsequence. In some embodiments, the referred quality is related for example to, but not limited to, the signal-to-noise ratio of the individual images of the second sequence of images. In another embodiment this relates to a similarity of images in the first sequence of images with the desire to reduce the impact of apparent object motion on the second sequence of images, resulting in a less motion perturbed second sequence of images.

According to a further embodiment of the present disclosure, the processing unit is configured for generating the second sequence of tomographic optoacoustic images based on an analysis of tomographic optoacoustic images of the first sequence of tomographic optoacoustic images using a feature tracking algorithm by means of which a temporal behavior of one or more individual contributions, e.g. an imaged part of the object, to tomographic optoacoustic images of the first sequence is analyzed and/or tracked. By this means, a time-dependent individual contribution of an imaged part of the object can be identified and its influence on the images, such as the image quality, can be reduced or eliminated in a reliable and efficient manner.

In some embodiments, the processing unit is configured for generating the second sequence of tomographic optoacoustic images based on an analysis of statistical properties of tomographic optoacoustic images of the first sequence of tomographic optoacoustic images. Alternatively or additionally, the processing unit is configured for processing the second sequence of tomographic optoacoustic images based on an analysis of statistical properties of tomographic optoacoustic images of the second sequence of tomographic optoacoustic images. In some embodiments, the analysis of statistical properties comprises a separation of the tomographic optoacoustic images of the sequence of tomographic optoacoustic images into contributing components, for example by means of at least one of a principal component analysis (PCA), an independent component analysis (ICA), a multi-variant data analysis, a vortex component analysis (VCA), a matrix factorization, a fitting procedure, a deconvolution procedure, an image co-registration algorithm, a moving average processing or a selective frame dropping processing. The analysis of statistical properties provides a highly expressive basis for processing the first sequence of images, for example for deriving the second sequence of images from the first sequence of images so that a high frame rate second sequence of images exhibiting high quality is obtained.

In another embodiment the image acquisition unit is configured to utilize photon absorption information from previous tomographic optoacoustic images of the same object to assess and/or change or adjust an amplification of signals corresponding to acoustic waves originating from deeper inside of the object in order to correct for reduced light fluence in deep tissue. By means of this embodiment, current images obtained from an object can be corrected in order to eliminate or reduce adverse effects due to a decrease of light fluence in increasing depths within the object, wherein the relevant information, on which the correction of the current images is based, is determined from previously acquired images. Because the relevant information preferably relates to absorption properties of the object, the relevant information is called absorption information. In total, also this embodiment contributes to further increased image quality of the high-rate video sequences obtained with the present disclosure. For example, this is due to the increased dynamic range on the analog-to-digital conversion in deeper regions of the object, where emitted acoustic waves are weaker due to the attenuation of the exciting radiation in the object.

In some embodiments the processing unit is configured for generating the second sequence of tomographic optoacoustic images by selecting and/or discarding individual tomographic optoacoustic images of the first sequence of tomographic optoacoustic images based on the analysis of the one or more tomographic optoacoustic images of the first sequence of tomographic optoacoustic images. In some instances, the processing unit is configured for generating a replacing tomographic optoacoustic image which is inserted into the second sequence of tomographic optoacoustic images in the case that a tomographic optoacoustic image of the first sequence of tomographic optoacoustic images has been discarded, wherein the replacing tomographic optoacoustic image is generated based on two or more preceding and/or following images, for example, by interpolating and/or extrapolating the preceding and/or following images, of the first sequence of tomographic optoacoustic images being adjacent to the discarded tomographic optoacoustic image. These embodiments represent, alone or in combination, a very simple and reliable way in order to improve the image quality, for example, with respect to motion artifacts and/or noise, of the second sequence of images.

According to another embodiment of the present disclosure, the processing unit is configured for generating the second sequence of tomographic optoacoustic images by moving averaging of tomographic optoacoustic images of the first sequence of tomographic optoacoustic images, wherein each time at least two subsequent tomographic optoacoustic images of the first sequence of tomographic optoacoustic images are averaged, whereby a SNR improvement of the images is obtained. This approach is of particular interest when images are acquired at a very high image rate, for example in deep penetration optoacoustic imaging. In some cases, a reduction of the temporal resolution and blurring of the image may occur, e.g. in motion-rich settings. These effects can be, however, efficiently and reliably corrected or eliminated by means of the present disclosure and the various embodiments.

According to a further embodiment of the present disclosure, the at least one property of the acquisition unit, on which the derivation of the second sequence of images from the first sequence of images is based, relates to an intensity of the electromagnetic radiation with which the object is excited while acquiring the first sequence of tomographic optoacoustic images. By this means, in the generation of the second sequence of images from the first sequence of images conditions of the acquisition unit, i.e. the illumination intensity, while images of the first sequence were acquired are considered, which allows for an even better and reliable generation of a high-rate second sequence of images exhibiting high quality. In one embodiment this additional information may be used to amplify or weight the image of the first sequence in its contribution to the second sequence of images. In another embodiment, this information can also be used as an additional quality metric for assessing the individual properties of the images of the first sequence of images. This is based on the assumption that the noise floor of the acquisition unit is static, while the photoacoustic signal relates linearly to the incident radiation, resulting in a higher signal-to-noise ratio for images acquired at increased radiation intensity.

According to a an embodiment, the illumination device is configured for illuminating the object with electromagnetic radiation at multiple wavelengths and the processing unit is configured for analyzing the first sequence and/or the second sequence of tomographic optoacoustic images at the multiple wavelengths. This particularly advantageous approach is also referred to as multispectral optoacoustic imaging (MSOT), wherein multispectral processing of the acquired image data of the first and/or second high frame rate video sequence is carried out by associating absorbers with individual pixels and thus allowing for localizing absorbers based on their spectral absorption profile over multiple excitation wavelengths. Because of the per-pixel evaluation, it may be configured to correct the acquired images for motion and noise to allow the so-called spectral unmixing algorithms to provide reliable spectrally-dependent information.

In a further embodiment the system comprises a display unit for displaying a video stream of the first sequence of tomographic optoacoustic images and/or the second sequence of tomographic optoacoustic images and/or a storage unit for storing the first sequence of tomographic optoacoustic images and/or the second sequence of tomographic optoacoustic images.

In an embodiment the second sequence of images is displayed in the form of individual images or a video, including real-time video. Real-time in the sense of the present disclosure relates to image frame rates of at least 10 image frames per second.

Moreover, features extracted or identified after processing of the first sequence of images may be further displayed on the display alone or superimposed on images and/or a video stream of the second sequence of images and/or of the first sequence of images. Superposition may be established by using a combination of grayscale and color representation. The term "features" in this context preferably relates to any information which is contained in the images and which can be identified in the processing step.

Preferably, also features which were extracted or derived by the processing unit from the first sequence of images can be displayed by the display unit, for example together with the video stream of the first and/or second sequence of images. The extracted features can relate, e.g., to a respiration frequency of the object, a temporal behavior of optoacoustic signals in dependence of the presence of a contrast agent within the object or a difference image. For example, the extracted or derived features are displayed by the display unit as a graph indicating dynamic changes of tracked components and/or a graph indicating dynamic changes of individual pixels and/or a graph or parametric map of at least one established biological kinetic parameter which has been derived from changes in pixel values.

For example, with a typical pharmacokinetic curve that starts at a concentration value and picks up for a certain period of time, the so-called rise time, to a peak value, so-called peak enhancement, respective biological kinetic parameter relate to at least one of:
  Cmax (peak enhancement, maximum concentration, e.g. absorption and/or concentration at the peak time point is 2.5 fold enhanced as compared to the baseline),
  area under the curve (AUC), i.e. an integral under the above-mentioned curve,
  Tmax (rise time, time to peak, i.e. time from start of injection to peak point),
  uptake rate (maximum slope, wash-in rate, steepness of rising slope of the curve),
  clearance rate (elimination rate, i.e. rate at which the substance is removed from the blood stream, steepness of dropping slope),
  perfusion index (AUC/Tmax),
  half-life (i.e. time to half elimination) or rates resulting from modeling of rate constants in different compartmental models of varying complexity.

In some instances, the display unit is designed to display overlay images or overlay sequences of images, wherein at least two different kinds of images are displayed in a superposition. For example, anatomical images of the object are superimposed with molecular-specific images of the object. Likewise, a sequence of anatomical images can be overlaid with a sequence of molecular-specific images. By means of this representation of the image information extracted by means of the processing and/or analyzing steps according to the present disclosure, a high degree of additional diagnostically conclusive information is provided.

In some embodiments, the image acquisition unit is designed as a handheld device and/or a portable device and/or an endoscopic device. In most situations or cases of handheld, portable and/or endoscopic applications, there is a certain relative movement between the image acquisition probe, i.e. the image acquisition unit, and the object. Therefore, the present disclosure is of particular advantage in combination with these applications, because possible motion-related artifacts in the sequences of images can be easily and reliably reduced or eliminated.

In the following, further embodiments for suppressing background noise and artifacts in the images of the first sequence of images will be described.

For example, a movement of the image acquisition unit relative to the object or a movement of the object relative to the image acquisition unit is detected or tracked, e.g. by means of a mechanical or optical sensor in the, preferably handheld or portable, image acquisition unit. Based on this information, a noise reduction or noise rejection can be performed, e.g. by means of a correlation between sequential and/or time-spaced frames.

Alternatively or additionally, a controlled relative motion between the object and the image acquisition unit can be induced intentionally. In this way, noise becomes un-correlated while SNR becomes improved by exploitation of the effect that image signals will always appear in a position corresponding to the induced (or captured) motion, whereas noise, and for example, artifacts and reflections, will appear in positions which will have a random distribution and therefore can be filtered out by cross-correlation, un-mixing of time components and similar methods.

It will be readily understood by one of skill in the art having the benefit of this disclosure that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

Figure 1:
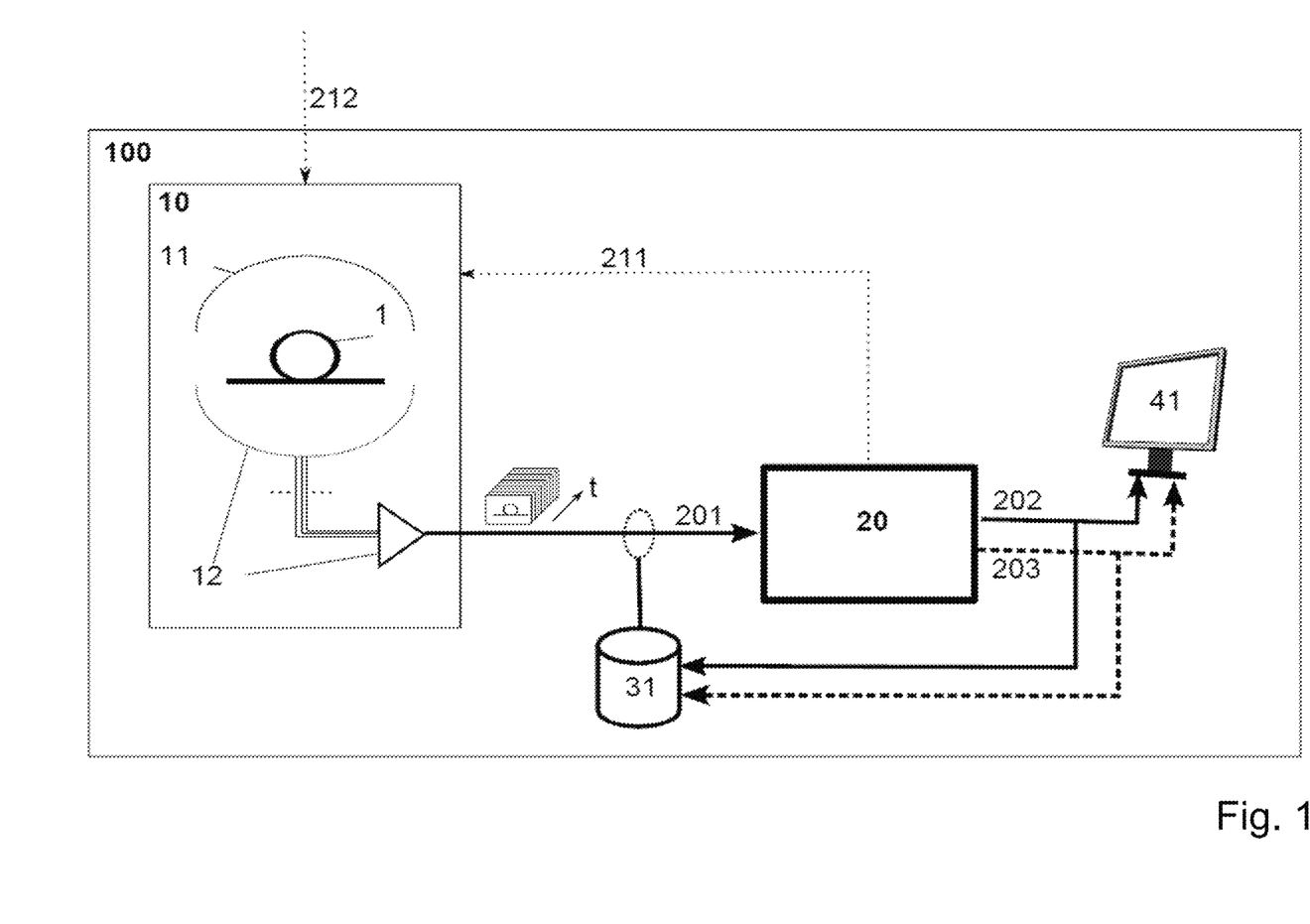
FIG. 1 shows a schematic representation of a system according to the present disclosure.

FIG. 1 shows a schematic representation of the system 100 according to the present disclosure. The system 100 comprises an image acquisition unit 10 for acquiring images of an object 1, which can be preferably be a biological tissue, a processing unit 20, a storage unit 31 and a display unit 41.

The image acquisition unit 10 comprises an illumination device 11 for, for example, uniformly, illuminating the object 1 in a desired imaging region by pulsed or frequency modulated laser light.

The image acquisition unit 10 further comprises a detection device 12 for capturing ultrasound waves generated in a three-dimensional imaging region of the object 1 upon illumination. The detection device 12 comprises an array of ultrasound detection elements, wherein the number of detector elements and/or the area covered by the array of detector elements are dimensioned such that ultrasound waves emanating from the whole imaging area of the object 1 can be detected simultaneously. This allows for creating a full tomographic optoacoustic image from the acquired ultrasound waves for each of the illumination pulses, so that acoustic waves are collected repeatedly and a first video sequence 201 of respective tomographic optoacoustic images is obtained, wherein each of the illumination pulses serves as a frame, i.e. a time frame, of the first video sequence 201 of the tomographic optoacoustic images.

It should be noted that power fluctuations in the excitation chain, i.e. the illumination device 11, of the system 100 may contribute to noise signals, wherein, dependent on the utilized technology, the power of the illumination device 11, for example, the laser power, can vary from pulse to pulse and can thus can have an impact on the information contained and/or displayed in the final image. However, in many settings this impact can be corrected by using laser integrated power measurement devices and a dependent amplification of the detected optoacoustic signals in terms of low power pulses. Such measurements can also be used as a metric to select or weigh frames in one of the algorithms described below in more detail.

In the processing unit 20 the first video sequence 201 of tomographic optoacoustic images is analyzed and/or processed according to the present disclosure, for example, by effecting analyzing and/or processing steps according to the various embodiments of the present disclosure. The output of the processing unit 20 is a second video sequence 202 of tomographic optoacoustic images exhibiting improved properties as well as so-called metadata 203 of various kinds, for example images, values or graphs.

In the storage unit 31 the first video sequence 201 of tomographic optoacoustic images and/or the improved second video sequence 202 of tomographic optoacoustic images and/or the metadata 203 generated by the processing unit 20 can be stored.

In the display unit 41 the first video sequence 201 of tomographic optoacoustic images and/or the improved second video sequence 202 of tomographic optoacoustic images and/or the metadata 203 generated by the processing unit 20 can be displayed.

Figure 2:
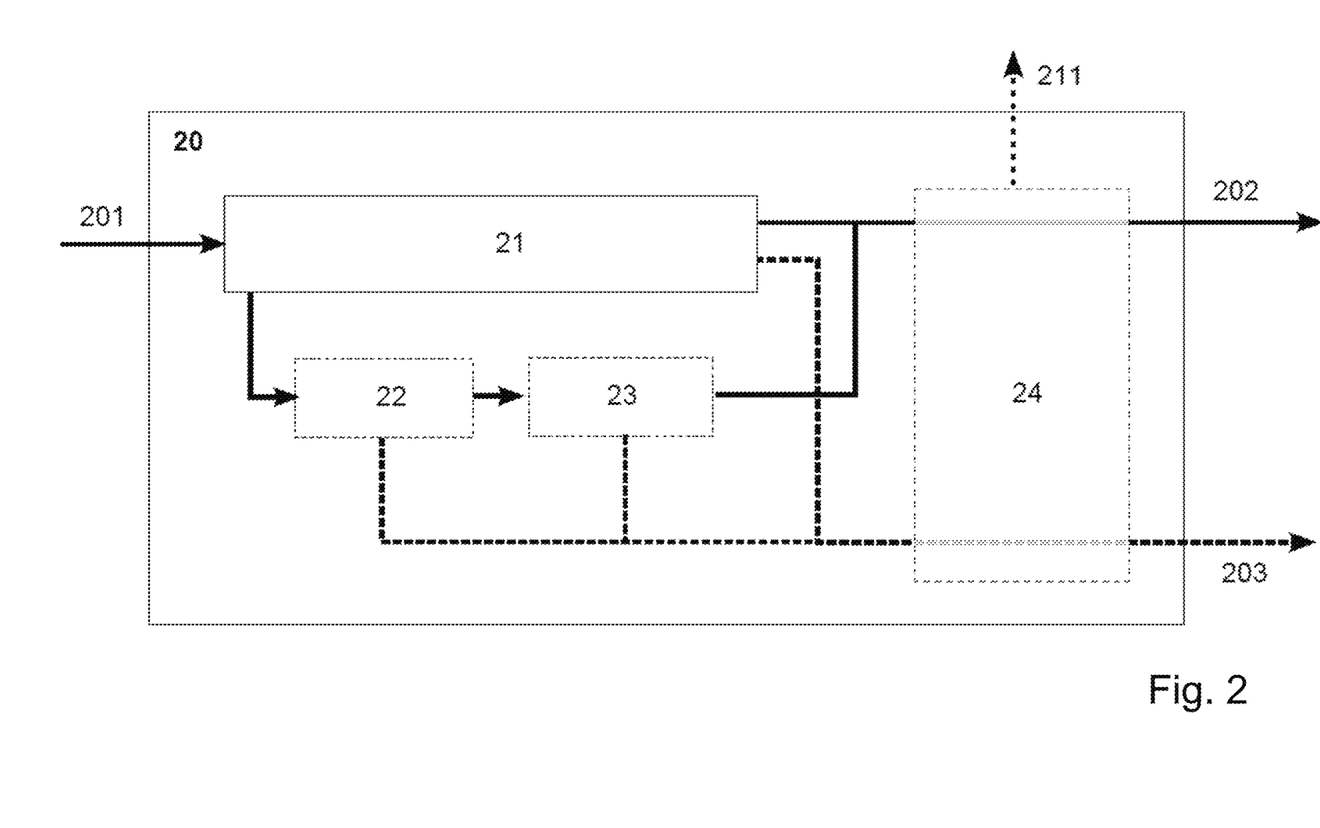
FIG. 2 shows a schematic representation of a processing unit.

FIG. 2 shows a schematic representation of the processing unit 20 shown in FIG. 1. The processing unit 20 comprises a core processor 21 that performs the analyzing and/or processing operations on the first video sequence 201 of tomographic optoacoustic images according to the present disclosure including various embodiments thereof.

Preferably, the processing unit 20 comprises a frame component analysis device 22 for analyzing the first video sequence 201 of tomographic optoacoustic images with respect to contributing components. Moreover, the processing unit 20 preferably comprises a frame component correction device 23 for correcting components contributing to tomographic optoacoustic images of the first sequence 201 and for generating the second video sequence 202 of tomographic optoacoustic images exhibiting increased quality, wherein the generation of the second video sequence 201 is based on the result of the correction of components contributing to tomographic optoacoustic images of the first sequence 201.

The core processor 21 and/or the frame component analysis device 22 and/or the frame component analysis device 22 also generate metadata 203, such as images, values and graphs, which describe or relate to phenomena in the first video sequence of tomographic optoacoustic images.

In a further embodiment, the output of the core processor 21 and/or the frame component analysis device 22 and/or the frame component analysis device 22 can optionally be analyzed by a data analysis device 24, by means of which the metadata 203 can be further enriched.

In the following, further aspects of the present disclosure as well as further aspects of various embodiments of the present disclosure are described by referring to FIGS. 1 and 2.

The optoacoustic imaging system 100 is able to acquire, store and process a time series of two or three dimensional tomographic video images of the same area in the imaged object 1 at a high frame rate using stationary illumination 11 and detection devices 12, allowing for the use of algorithms for improving SNR and coping with motion artifacts. Fast image generation is enabled by pulsed excitation, where each pulse generates an instantaneous snapshot image.

Because ultrasonic responses generated by the pulsed illumination are comparatively weak and undergo further attenuation when traveling to the detector through tissue and water, the use of single pulse image frames would provide only a limited amount of measurement data points available without any redundancy to cope for bad signals, as any noise in system and acquisition is added individually on top of the captured data.

In order to improve SNR and to cope with motion artifacts, multiple repeatedly acquired images are analyzed and/or processed according to the present disclosure such that the quality of the individual images is improved while the effective frame rate is kept high, i.e. at a maximum, and thus the usability for imaging fast processes in the object is maintained.

This allows for investigating high-resolution changes of optical contrast features of the same area inside the imaged object and fast processes in living organisms that cannot be revealed by other imaging modalities.

Exemplary frame rates in order to be able to fulfill the aforementioned aims start from 10 frames per seconds. Upper bounds to the frame rate are only given by hardware limitations such as repetition rate of the excitation source or data rate of processing systems.

Excitation is delivered using preferably uniformly distributed illumination 11 of the imaging region of the object 1. It can either be of pulsed nature with pulse widths in the order of nanoseconds, or of continuous nature with either frequency or intensity modulation applied. In any of the mentioned cases the illumination wavelength can optionally be configured in the course of the measurement at any given rate.

The stationary optoacoustic detector array 12 can be of any curved or linear shape that can acquire acoustic waves from sufficient projections of the imaged object 1 for any imaging instant in order to make time consuming mechanical detector movements unnecessary.

Another aspect of the present disclosure relates to the high data rate processing unit 20 which is connected with the image acquisition unit 10, in particular with the detection device 12, and which provides computational power and algorithms to capture and analyze and/or process the first video sequence 201.

In some instances the signals of sufficient or ideally all detectors of the array 12 can be captured in one acquisition cycle. Apart from individual processing algorithms it is an object of the present disclosure to analyze a time series, i.e. a sequence 201, of images and identify extrinsic, parasitic influences such as noise and motion that deteriorate the individual video frames.

In an exemplary manifestation, a moving average processing on the first video sequence 201 of images can be executed in order to remove independent influences while retaining the effective video frame rate.

Other aspects include a selection process in which the quality of individual video frames by using metrics, such as blur, mutual information, similarity or image correlation, is assessed. Based on these metrics, i.e. criteria, it is an option to discard individual, highly noise or motion affected video frames completely in order to increase overall quality and signal to noise ratio as a trade-off with retained information frame rate. This allows amendment of the captured first video stream 201 to an improved, final second video stream 202.

In another aspect, temporal patterns of individual contributions to the content of the individual images of the first video sequence 201 can be used in the frame component analysis device 23 to both classify the contributions and retrieve information about change processes in the images that might themselves be important aspects of the measurement. This may include periodic motion patterns, such as the breathing rate of an animal that leads to repeated, periodic contractions of the rib cage and represents a major source of motion and can thus be progressively used in processing both past and future video frames.

If calculated online during the measurement in the data analysis device 24, this also allows for capturing health indicators such as breathing or heart rate as well as a metric for motion of the detection device 12 and thus image reliability in handheld imaging. Therefore, in an embodiment of the system according to the present disclosure, the detection device 12, and optionally the illumination device 11, is or are integrated in a handheld probe which can be grasped or touched by hand and, e.g., positioned onto the surface of an object under investigation, e.g. a patient.

This information, for example, relating to breathing, heart rate, blood flow or motion of the object 1 and/or motion of the detection device 12, when captured and processed in real time can also be used in a feedback loop 211 as a control data for the image acquisition unit 10. For example, by means of information relating to breathing or heart rate of the object 1 or relative motion between the object 1 and the image acquisition unit 10 a corresponding feedback signal is generated and fed to the image acquisition unit 10, wherein the image acquisition unit 10 is controlled by the feedback signal such that, e.g., optoacoustic images are only acquired at certain time frames or times of the breathing cycle, cardiac cycle or blood circulation.

The acquired and/or derived data can be stored in the storage device 31. Image data relating to sequences of tomographic optoacoustic images can be stored before (first sequence 201) any processing steps and/or after (second sequence 202) processing in the processing unit 20. Moreover, also additional metadata 203 generated in the course of processing can also be stored in the storage device 31.

The stored data can be analyzed immediately or at a later point in time by the data analysis device 24. In a real time processing enabled system, the processed second sequence of images and/or the unprocessed first sequence of images, so-called raw data, can also be visualized on the display device 41.

Noise and motion correction of the images of the first sequence 201 is especially advantageous when high speed changes in contrast need to be tracked that cannot be revealed using mechanisms that reduce the frame rate of the acquired data. Examples are fast changes in contrast when perfusing biological tissue with a marker substance, where certain image features increase in signal.

According to the present disclosure, the generation of the second high frame rate video sequence 202 of images of absorbing structures is achieved by means of a post-processing of the first high frame rate video sequence 201 of the acquired images. Here, a certain task is multispectral processing of the acquired image data of the first high frame rate video sequence 201 by associating absorbers with individual pixels and thus allowing for localizing absorbers based on their spectral absorption profile over multiple excitation wavelengths. This approach is often referred to as multispectral optoacoustic imaging (MSOT). Because of the per-pixel evaluation it is essential to correct the acquired images for motion and noise to allow the so-called spectral unmixing algorithms to work.

According to an embodiment of the present disclosure, the acquisition in the described high speed measurement system 100 can optionally be triggered using external device (not shown) by means of which at least one property of the object 1 relating to temporal, for example, periodic, changes at or within the object 1 can be acquired while the first sequence of tomographic optoacoustic images is acquired. Temporal changes may comprise, e.g., changes due to respiration, pulse or blood flow. The external device is designed to produce an according control signal 212 for controlling the image acquisition unit 10. For example, the external device can be an electrocardiogram (ECG) or a breathing rate monitoring system by means of which the image acquisition can be triggered, for example, started, in motion-free moments between breathing cycles or at certain moments in the cardiac cycle to further increase the image quality.

In the following, further embodiments of the present disclosure will be discussed.

In one embodiment, the optoacoustic detection device 12 encircles the object 1 in a full or partial circle or arc. By means of focusing the sensitivity of the individual detector elements of the array in a direction perpendicular to the imaging plane, the imaged area is thus restricted to signals emitted in a quasi two-dimensional plane. If focusing is reduced or completely omitted, signals are captured from the whole three-dimensional area enclosed by the detection device 12.

The illumination device 11 irradiates laser pulses onto an area of the object 1 being slightly larger than the imaging plane in order to provide uniform illumination of the whole imaging area. Detection device 12 and illumination device 11 are preferably static with respect to each other, in order to allow for repeated imaging of the same area without a change in the setting.

The object 1 can be translated perpendicular to the imaging plane to select the area to image. By means of this setup it is possible to generate high frame rate data of one imaging area. Multiple imaging areas can be covered by fast translation of the object 1, or additional detection and illumination device pairs 12/11 that operate independently. Exemplary applications of this embodiment are preclinical imaging of small animals or clinical imaging of peripherals, such as hand, finger or feet.

An important step in improving the quality of the final video stream 202 in the core processing device 21 is the assessment of the quality of the individual frames, as this allows for subsequent, quality-dependent processing of the input data 201. In this embodiment, the quality improvement of the output video stream 201 is achieved by elimination of low quality video frames, which improves the overall quality of the video. This is mainly appropriate with high video frame rates, where processing time is very important. As a decrease in frame rate, or a varying frame rate in general is not desirable in most applications, frames that are dropped due to their insufficient quality are substituted by interpolating and/or extrapolating the neighboring good frames.

In order to assess the quality of a video frame, two different types of video frame metrics, i.e. criteria, can be applied: First, individual image metrics on the one hand assess the quality of the frame only with respect to itself. Examples include image SNR with respect to background area, contrast and different blur and sharpness related metrics. Second, mutual metrics on the other hand classify an image with respect to other images. Standard deviation, k-means, similarity, image correlation and mutual information based on both intensity and feature-based metrics are examples. They are very advantageous for the quality improvement in motion-perturbed measurements as they allow for identifying video frames acquired at time points with corresponding positions of the object 1.

Depending on the pro-rata contributions of motion and noise to the acquired video, a number of reasonable metrics need to be combined. Individual image metrics can identify noisy frames, while mutual metrics help to find frames that show the same setting to help identify motion compensated frames. In the case of preclinical imaging with small animals, this is largely dependent on the region that is measured.

As additional information, the metrics for the individual frames are provided as metadata 203 on the output of the processing device. This allows for user feedback on the quality of the video stream.

This advantageously enables the per-pixel monitoring of even small intrinsic contrast changes in the measured subject which would have otherwise been hidden and obscured by noise and motion. An example of such fast change is the change in blood oxygenation as the oxygen content in the breathing air supply of a live animal or human is changed. This allows judgment of the degree of vascularization and thus blood perfusion in tissue.

In a further embodiment, the video frame images are processed using statistical metrics in the frame component analysis device 22. The input to this step can either be the original first video stream 201, or the second video steam 202 already pre-processed by the core processing device 21. The incoming video stream 201 is separated in contributing components using methods of blind source separation or equivalent approaches. A method that has proven efficient and robust is principal component analysis (PCA) that relies on orthogonality of contributing components, but comparable algorithms from that domain can work equally well. The resulting components are then classified into actual signal sources, meaning actual changes in contrast in certain pixels, and unwanted contributions such as motion and noise. As these methods include an indicator on the temporal behavior of a contribution, this can be used in the frame component correction device 23 to identify noise and motion as these usually show a very high frequent behavior, while changes in signal are assumed to be relatively slow changing in comparison with a significant trend.

While this differentiation is very simple for the human eye by looking either at the moving component picture or its temporal profile, an automatic decision process needs to take into account various parameters. Essential are means of Fourier transform or similar, which visualize the frequency content in individual components and an evaluation of the mean contribution and the significance in relation to the complete video stream.

Depending on the application it is important to define the respective thresholds to separate slow varying signal components from usually more high frequent motion and noise components. A-priori knowledge of patterns can also be applied using fitting and deconvolution procedures or tracking algorithms. With this differentiation into perturbations and actual signal being made, the correction device 23 can re-assemble a final video stream 202 that is free of the unwanted contributions of noise and motion.

The separation into components also allows further, even more simple processing tasks such as smoothening or selective filtering on the individual components. As an example, a moving average processing step on components representing ideal white noise would automatically lower their influence and thus improve from the dataset without further actions being necessary.

The extracted meta content or meta data 203 retrieved from the separation in the frame component analysis device 22 can serve to identify patterns in the motion or noise components, that can be provided as a visual feedback, i.e. displayed in display 41, in addition to the final video stream 202. This is not restricted to the temporal profiles of certain contributions, but also their localization. This possibility to reveal and analyze spatio-temporal events with optical contrast enables very powerful applications.

In another embodiment, binning procedures to separate frames, i.e. images, based on a certain stadium can be applied in the data analysis device 24 using mutual video frame metrics to identify different groups of frames. One example is the separation of heartbeat cycle into systolic and diastolic segments that can help create high quality snapshots in a motion-rich scenario.

In a further embodiment, the output of the frame component analyzing device 22 can help in the data analysis device 24 to identify physiological parameters of the imaged object 1 by analyzing the temporal profiles of certain contributors. This includes breath rate and heart rate recognition based on motion components, as these are periodic changes in the video streams 201 and/or 202.

In a real-time system 100, the physiological parameters of the imaged object 1 can in turn be used in a feedback loop as a control signal 211 which triggers the image acquisition unit 10 in moments with predicted low motion, e.g. in between breathing cycles.

In yet another aspect of the present disclosure, the output video images 202 can be evaluated for dynamic changes within the entire images or certain pixels in the processing unit 20. This allows for visualization of changes either as a graph or as a parameter map indicating parameters characterizing the change in value of a certain pixel by either plain observation or some pharmacokinetic modeling. This allows for utilizing the image acquisition unit 10 as a device which enables visualizing a bio-distribution of injected agents and modeling their kinetic behavior within the imaging region.

Parameters to be observed may include, but are not limited to, peak enhancement, area under the curve, rise time, time to peak, wash-in rate or perfusion index, mean residence time, volume of distribution, clearance, CMax, TMax, bioavailability and various rate constants that allow fitting a pharmacokinetic model. Regarding these parameters it is referred to respective detailed elucidations and examples given above.

Depending on the specific kinetics of interest, this may be applied to single wavelength video sequences or multispectral video sequences, wherein the latter allow for assessment of biological properties of tissue and organ function, where there is currently no other imaging modality that can deliver equally high frame rates with functional contrast.

In another embodiment, the illumination wavelength can be changed during the acquisition, so that illumination pulses of different wavelength capture different contrast inside the imaged object to further enrich the dataset in another dimension, i.e. by a spectral dependence of the optoacoustic image data. This features the powerful tool of Multispectral Optoacoustic Tomography (MSOT) that has been previously used on static settings to reveal absorbers based on their absorption profile. With an interleaved processing of the individual frames acquired at different wavelengths, the aforementioned features can be applied to hugely improve the possibilities for fast MSOT for which motion-free data sets to characterize the absorption spectrum of individual pixels are essential. Here, the MSOT benefits significantly from improved quality of the video stream 202 obtained by means of the present disclosure. Another important benefit in employing this method lies in the ability to trace contrast changes also if they are caused by multiple absorbers. As an example, a labeled drug to increase blood circulation could produce contrast in a decisive wavelength where the attached contrast agent absorbs, but also change the amount and thus the absorption by blood.

In another embodiment, an optional compression step can be incorporated in the course of video frame processing in order to simplify data transfer and reduce storage space. This compression can either happen in a combined processing step as a side product of any of the algorithms employed, or in a subsequent step using commonly known data or video compression mechanisms.

In yet another embodiment, the detection device 12 collects data from a three dimensional volume within the object 1 from only one side of the object 1. Detection elements are either arranged on parts of a sphere in order to allow focusing on the imaging area, or in a linear manner in order to cover a broader and less wide area with substantially less or no focusing. In most applications it makes sense to arrange illumination device 11 and detection device 12 on the same side of the object 1—however a uniform illumination of the imaging area needs to be granted, and still the illumination device 11 needs to be fixed with respect to the detection device 12. This arrangement allows for greater flexibility in selecting the imaging area and mounting in a handheld device. In handheld operated mode however, the imaging rate needs to be very high in order to fulfill the requirement of a quasi-static setting. In general, the detection geometry of this embodiment allows for whole body small animal imaging and handheld clinical imaging.

In another embodiment, the described imaging system can be applied to humans using either handheld or endoscopic imaging by modifying the acquisition device 10 accordingly.

Dependent on the acquisition rate the system supports, some or all components of the processing unit 20 detailed above may need to be implemented in dedicated hardware to achieve the necessary throughput.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A system configured for optoacoustic imaging of an object, the system comprising:
  an image acquisition unit configured for acquiring a first sequence of tomographic optoacoustic images of a region of interest of the object, the image acquisition unit comprising:
    an illumination device configured for irradiating the region of interest of the object with electromagnetic radiation, and
    a detection device configured for repeatedly collecting acoustic waves emerging from the object upon irradiating the object and configured for generating the first sequence of tomographic optoacoustic images of the region of interest from the repeatedly collected acoustic waves; and
  a processing unit that generates a second sequence of one or more tomographic optoacoustic images from the first sequence of tomographic optoacoustic images based on at least one of the following:
    an analysis of one or more tomographic optoacoustic images of the first sequence of tomographic optoacoustic images with respect to individual properties of the one or more tomographic optoacoustic images, and
    an analysis of properties of the repeatedly collected acoustic waves prior to generating the first sequence of tomographic optoacoustic images from the repeatedly collected acoustic waves.

2. The system according claim 1, wherein the processing unit generates the second sequence of one or more tomographic optoacoustic images from the first sequence of tomographic optoacoustic images further based on at least one property of the object while acquiring the first sequence of tomographic optoacoustic images, and wherein the at least one property of the object relates to temporal changes at or within the object while acquiring the first sequence of tomographic optoacoustic images.

3. The system according to claim 1, wherein the processing unit generates the second sequence of one or more tomographic optoacoustic images from the first sequence of tomographic optoacoustic images further based on at least one property of the object while acquiring the first sequence of tomographic optoacoustic images, and wherein the at least one property of the object is acquired by an external device configured for observing temporal changes at or within the object.

4. The system according to claim 1, wherein the processing unit generates the second sequence of one or more tomographic optoacoustic images from the first sequence of tomographic optoacoustic images further based on at least one property of the object while acquiring the first sequence of tomographic optoacoustic images, and wherein the at least one property of the object is derived from one or more tomographic optoacoustic images of the first sequence of tomographic optoacoustic images.

5. The system according to claim 1, wherein the processing unit is configured for generating the second sequence of tomographic optoacoustic images based on an analysis of a subsequence of tomographic optoacoustic images of the first sequence of tomographic optoacoustic images.

6. The system according to claim 1, wherein the processing unit is configured for generating the second sequence of tomographic optoacoustic images based on an analysis of tomographic optoacoustic images of the first sequence of tomographic optoacoustic images regarding properties of the tomographic optoacoustic images with respect to each other.

7. The system according to claim 1, wherein the processing unit is configured for generating the second sequence of tomographic optoacoustic images based on an analysis of tomographic optoacoustic images of the first sequence of tomographic optoacoustic images using a feature tracking algorithm by which a temporal behavior of one or more individual contributions to tomographic optoacoustic images of the first sequence is analyzed.

8. The system according to claim 1, wherein the processing unit is configured for generating the second sequence of tomographic optoacoustic images based on an analysis of statistical properties of tomographic optoacoustic images of the first sequence of tomographic optoacoustic images.

9. The system according claim 8, wherein the analysis of statistical properties comprises a separation of the tomographic optoacoustic images of the sequence of tomographic optoacoustic images into contributing components.

10. The system according to claim 1, wherein the processing unit is configured for processing the second sequence of tomographic optoacoustic images based on an analysis of statistical properties of tomographic optoacoustic images of the second sequence of tomographic optoacoustic images.

11. The system according to claim 1, wherein the acquisition unit is configured to be controlled by control signals from at least one of the following:
the processing unit and
an external device, which is configured for observing a time-variant process in the object;
wherein the acquisition unit is configured for acquisition of the first sequence of tomographic optoacoustic images at less motion-perturbed instants.

12. The system according to claim 1, wherein the image acquisition unit is configured to utilize photon absorption information from previous tomographic optoacoustic images of the same object to change amplification of signals corresponding to acoustic waves originating from deeper inside of the object in order to correct for reduced light fluence in deep tissue.

13. The system according to claim 1, wherein the processing unit is configured for generating the second sequence of tomographic optoacoustic images by selecting and discarding individual tomographic optoacoustic images of the first sequence of tomographic optoacoustic images based on the analysis of the one or more tomographic optoacoustic images of the first sequence of tomographic optoacoustic images.

14. The system according to claim 13, wherein the processing unit is configured for generating a replacing tomographic optoacoustic image which is inserted into the second sequence of tomographic optoacoustic images in the case that a tomographic optoacoustic image of the first sequence of tomographic optoacoustic images has been discarded, wherein the replacing tomographic optoacoustic image is generated based on at least one of two or more preceding and following images of the first sequence of tomographic optoacoustic images being adjacent to the discarded tomographic optoacoustic image.

15. The system according to claim 1, wherein the processing unit is configured for generating the second sequence of tomographic optoacoustic images by moving averaging of tomographic optoacoustic images of the first sequence of tomographic optoacoustic images, wherein each time at least two subsequent tomographic optoacoustic images of the first sequence of tomographic optoacoustic images are averaged.

16. The system according to claim 1, wherein the at least one property of the acquisition unit relates to an intensity of the electromagnetic radiation with which the object is irradiated while acquiring the first sequence of tomographic optoacoustic images.

17. The system according to claim 1, wherein the illumination device is configured for irradiating the object with electromagnetic radiation at multiple wavelengths and the processing unit is configured for analyzing at least one of the following: the first sequence and the second sequence of tomographic optoacoustic images at the multiple wavelengths.

18. The system according to claim 1, comprising:
a display unit configured for displaying a video stream of at least one of the following: the first sequence of tomographic optoacoustic images and the second sequence of tomographic optoacoustic images.

19. The system according to claim 1, comprising:
a storage unit configured for storing at least one of the following: the first sequence of tomographic optoacoustic images and the second sequence of tomographic optoacoustic images.

20. The system according claim 1, wherein the image acquisition unit comprises a handheld device.

21. A method for optoacoustic imaging of an object by acquiring a first sequence of tomographic optoacoustic images of a region of interest of the object, the method comprising:
irradiating the region of interest of the object with electromagnetic radiation;
repeatedly collecting acoustic waves emerging from the object upon irradiating the object and generating the first sequence of tomographic optoacoustic images of the region of interest from the repeatedly collected acoustic waves; and
generating a second sequence of one or more tomographic optoacoustic images from the first sequence of tomographic optoacoustic images based on at least one of the following:
an analysis of one or more tomographic optoacoustic images of the first sequence of tomographic optoacoustic images with respect to individual properties of the one or more tomographic optoacoustic images, and
an analysis of properties of the repeatedly collected acoustic waves prior to generating the first sequence of tomographic optoacoustic images from the repeatedly collected acoustic waves.

22. The system according to claim 1, wherein the analysis of the one or more tomographic optoacoustic images comprises an analysis of the one or more tomographic optoacoustic images with respect to at least one of the following individual properties of the one or more tomographic optoacoustic images: signal-to-noise ratio, contrast, blur, sharpness and histogram.

23. The system according to claim 1, wherein the analysis of properties of the repeatedly collected acoustic waves comprises an analysis of at least one of the following properties of the acoustic waves: signal-to-noise ratio, frequency spectrum and noise pattern.

24. The system according to claim 1, wherein the processing unit generates the second sequence of tomographic optoacoustic images from the first sequence of tomographic optoacoustic images by further considering at least one property of the acquisition unit while acquiring the first sequence of tomographic optoacoustic images.

25. The system according to claim 24, wherein the at least one property of the acquisition unit relates to a pulse-to-pulse variation of the power of electromagnetic radiation pulses with which the object is irradiated while acquiring the first sequence of tomographic optoacoustic images.

26. The system according to claim 25, wherein the generation of the second sequence of tomographic optoacoustic images from the first sequence of tomographic optoacoustic images by considering the pulse-to-pulse variation of the power of electromagnetic radiation pulses comprises an amplification of the collected acoustic waves emerging from the object upon irradiating of the object with low power pulses.

* * * * *

UNITED STATES PATENT AND TRADEMARK OFFICE
CERTIFICATE OF CORRECTION

PATENT NO.       : 9,551,789 B2
APPLICATION NO.  : 14/141773
DATED            : January 24, 2017
INVENTOR(S)      : Stefan Morscher et al.

It is certified that error appears in the above-identified patent and that said Letters Patent is hereby corrected as shown below:

Column 5, Line 10 reads, "…the object while the…" which should read, "…the object during the…"

Column 5, Line 34 reads, "…control signals from, wherein…" which should read, "…control signals, wherein…"

Column 5, Line 42 reads, "…heart cycle. By mean…" which should read, "…hear cycle. By means…"

Column 8, Line 59 reads, "…to a an embodiment,…" which should read, "…to an embodiment,…"

Column 13, Line 4 reads, "…video frames by using metrics,…" which should read, "…video frames, using metrics,…"

Column 15, Line 45 reads, "…is separated in contributing…" which should read, "…is separated into contributing…"

Column 15, Line 57 reads, "…show a very high frequent behavior,…" which should read, "…show a very high frequency behavior,…"

Column 16, Line 3 reads, "…more high frequent motion and…" which should read, "…more high frequency motion and…"

Column 18, Line 32 reads, "…system according claim 1,…" which should read, "…system according to claim 1,…"

Column 19, Line 18 reads, "…system according claim 8,…" which should read, "…system according to claim 8,…"

Column 20, Line 26 reads, "…system according claim 1,…" which should read, "…system according to claim 1,…"

Signed and Sealed this
Twenty-eighth Day of November, 2017

Joseph Matal
*Performing the Functions and Duties of the
Under Secretary of Commerce for Intellectual Property and
Director of the United States Patent and Trademark Office*